United States Patent
Young et al.

(10) Patent No.: US 6,925,868 B2
(45) Date of Patent: Aug. 9, 2005

(54) ACOUSTIC VOLUME INDICATOR

(75) Inventors: Winston B. Young, Monrovia, CA (US); Huey Wai, Monrovia, CA (US)

(73) Assignee: Young Manufacturing & Engineering, Inc., Monrovia, CA (US)

( * ) Notice: Subject to any disclaimer, the term of this patent is extended or adjusted under 35 U.S.C. 154(b) by 0 days.

(21) Appl. No.: 10/175,712

(22) Filed: Jun. 20, 2002

(65) Prior Publication Data

US 2003/0015036 A1 Jan. 23, 2003

Related U.S. Application Data

(60) Provisional application No. 60/300,335, filed on Jun. 22, 2001.

(51) Int. Cl.$^7$ .............................................. G01F 23/28
(52) U.S. Cl. ...................................... 73/290 V; 73/149
(58) Field of Search ........................ 73/579, 570, 149, 73/290 R, 290 V, 49.2, 32 A

(56) References Cited

U.S. PATENT DOCUMENTS

| | | | | |
|---|---|---|---|---|
| 2,667,782 A | * | 2/1954 | Shea ............................ | 73/149 |
| 2,924,096 A | * | 2/1960 | Humphres .................... | 73/149 |
| 3,413,847 A | * | 12/1968 | Kraushaar .................... | 73/149 |
| 3,596,510 A | * | 8/1971 | Paine et al. ................... | 73/149 |
| 3,624,828 A | * | 11/1971 | Edwards ....................... | 73/149 |
| 4,599,892 A | * | 7/1986 | Doshi .......................... | 73/49.2 |
| 4,635,487 A | * | 1/1987 | Gowing ................... | 73/864.62 |
| 4,715,221 A | * | 12/1987 | Grims et al. .................. | 73/149 |
| 4,991,433 A | * | 2/1991 | Warnaka et al. ........... | 73/290 V |
| 5,022,261 A | * | 6/1991 | Wolfson et al. ............... | 73/149 |
| 5,528,933 A | * | 6/1996 | Nemirow ...................... | 73/149 |
| 6,305,219 B1 | * | 10/2001 | Bentz et al. .............. | 73/290 V |
| 6,615,657 B2 | * | 9/2003 | Hongerholt et al. ...... | 73/290 V |

* cited by examiner

Primary Examiner—Helen Kwok
(74) Attorney, Agent, or Firm—Jeffer, Mangels, Butler & Marmaro LLP

(57) ABSTRACT

Acoustic volume indicators comprise a resonator, a frequency detector, and an indicator. The resonator can be an impactor or a vibration generator. The detector responds to vibration signals provided from the tank wall, which signals will show a significant increase in amplitude at the resonant frequency of the tank and its contents. The detector can be an accelerometer designed to record the received signal. The recorded signal is converted/analyzed by the frequency detector, and is compared to a known preprogrammed specific frequency vs. volume characteristic of the tank. Various audible and/or visual output or indicator devices can be used to indicate whether the liquid volume measurements within or outside of a predetermined volume range based on the known tank characteristics.

17 Claims, 2 Drawing Sheets

ACOUSTIC VOLUME INDICATOR

CROSS-REFERENCE TO RELATED APPLICATIONS

This application claims the benefit of U.S. Provisional application No. 60/300,335, filed Jun. 22, 2001.

FIELD OF THE INVENTION

This invention relates to devices for measuring the volume of liquid in a container and, more particularly, to devices designed for use in noninvasively measuring the volume of liquid in a tank where the liquid is separated from a gas, such as air, by means of a flexible diaphragm.

BACKGROUND OF THE INVENTION

The use of indicators to measure the volume of liquid in tanks is well known. Such indicators are typically of the invasive type, in that they are constructed to measure the volume or level of liquid in a tank through the use of one or more members that resides within the tank itself. Such invasive-type of liquid measuring device can include one or more members that is also disposed outside of the tank. Invasive measuring devices are adequate for use in applications where the tank is either not covered, or is covered but not pressurized.

Certain types of liquid handling containers are, however, pressurized for the purpose of performing a particular function. An example of such liquid handling container can be provided in the form of a hydraulic surge suppressor that comprises a pressurized diaphragm therein for the purpose of accommodating a pressure surge or hydraulic transient in the fluid line that it is attached to. In such an example application it is intended that the gas within the diaphragm be maintained under substantial pressure. For this reason, it is desired that there be no intrusive means for measuring the gas-to-liquid ratio, hence no perforations or holes in the walls of the tank, except for the inlet and outlet ports. This eliminates such obvious expedients as a sight glass, for example.

In U.S. Pat. No. 3,312,107, a method is taught for determining the amount of liquid in a tank by providing a swept frequency signal to excite an electromagnetic field within a metallic storage tank containing the liquid to be measured. The tank behaves as a resonant transmission type of cavity. When the sweep frequency signal equals one of the resonant frequencies of the tank, the signal is transmitted through the tank where it is detected at the output. Implementation of this measuring technique involves inserting a small coupling loop through the wall of the tank for exciting an electromagnetic field within the tank. A detector, such as a crystal, is coupled to the tank by means of another small coupling loop. The use of this device and method for measuring, of course, involves penetrating the wall of the tank at two points other than the inlet and outlet ports, which presents unwanted sealing problems.

In addition to the above requirements, for some locations it is desirable that the measuring instrumentation be sufficiently portable that it can be moved around to measure the liquid contents of a number of tanks. Alternatively, all or part of the instrumentation may be at least semi-permanently attached to the tank.

It is, therefore, desired that a device be constructed that is capable of providing an accurate measurement of liquid level within a liquid container in a non-invasive manner. It is desired that such device be capable of providing such volume measurement in volume containers that may or may not comprise a pressurized diaphragm or other type of pressurized member therein. It is further desired that such liquid volume device be somewhat portable so that it can be used to measure the liquid volume in more than one liquid container.

SUMMARY OF THE INVENTION

Acoustic volume indicators of this invention make use of noninvasive measuring techniques that involve the use of a resonating means for causing a liquid container to vibrate, a resonating detection means for receiving vibration data from the liquid container, frequency detection means for converting the vibration data to frequency and comparing the frequency to stored frequency v. volume data to obtain the liquid volume, and an indicator means for providing a desired output based on the liquid volume. The use of such acoustic volume indicator is especially well suited for use in measuring the liquid in a liquid container containing a pressurized diaphragm or bladder disposed therein, such as a hydraulic surge suppressor.

The resonating means can be provided in mechanical or electromechanical form. In an example embodiment, the resonating means is in the form of an impactor that is actuated to strike the side of the liquid container or tank by an actuator such as a solenoid device or the like. The impactor may strike the tank with an impulse to momentarily vibrate the tank. The resonating detection means can be in the form of a detector on the side of the tank that is designed to respond to vibrations signals provided from the tank wall, which signals will show a significant increase in amplitude at the resonant frequency of the tank and its contents. If the tank is known to resonate at a particular frequency when the tank is full of liquid, it will resonate at progressively higher frequencies as the amount of liquid decreases.

Alternatively, the resonating means can be provided in the form of an electromechanical vibration generator that is operated to generate a sweep frequency signal in the tank. A similar detector will respond to resonant frequencies as described above, a particular resonant frequency representing a certain amount of liquid in the tank.

Physically, it is preferable that the acoustic volume indicator be in the form of an electronic device which utilizes one of the above resonating techniques, and that is based on the characteristic that as the liquid volume in a tank increases, the natural frequency of the tank decreases. The resonating means may be either an impact plunger type or it may generate sweep frequency vibrations.

To record the vibration signal generated from the impulse generated, the detector can be in the form of an accelerometer having means to record the received signal. The recorded signal is than converted/analyzed by a frequency detection means, e.g., in the form of a microprocessor, into a frequency such as Fast Fourier Transform (FFT) which is then compared to a known preprogrammed specific frequency vs. volume characteristic of the tank. Various audible and/or visual output or indicator devices, such as a gauge or colored lights, may be used to display whether the liquid volume measurements are in or out of a predetermined volume range based on the known tank characteristics.

BRIEF DESCRIPTION OF THE DRAWINGS

This invention may be more clearly understood with reference to the following detailed description, and by reference to the following drawings in which.

DETAILED DESCRIPTION OF THE INVENTION

Acoustic volume indicators, constructed according to principles of this invention, are constructed for the purpose of enabling an accurate indication of liquid volume within a liquid container in a non-invasive manner, and operate on the principle that as the liquid volume in a tank increases, the natural frequency of the tank decreases. Acoustic volume indicators of this invention generally comprise a means for implementing or causing the liquid container to resonate, a means for detecting the resonation signal from the liquid container, a means for converting the detected resonation signal to a liquid level within the liquid container, and a means for displaying the liquid level and/or providing an audio and/or visual output signal in the event that the measured liquid level is different than a predetermined level.

Figure 1:
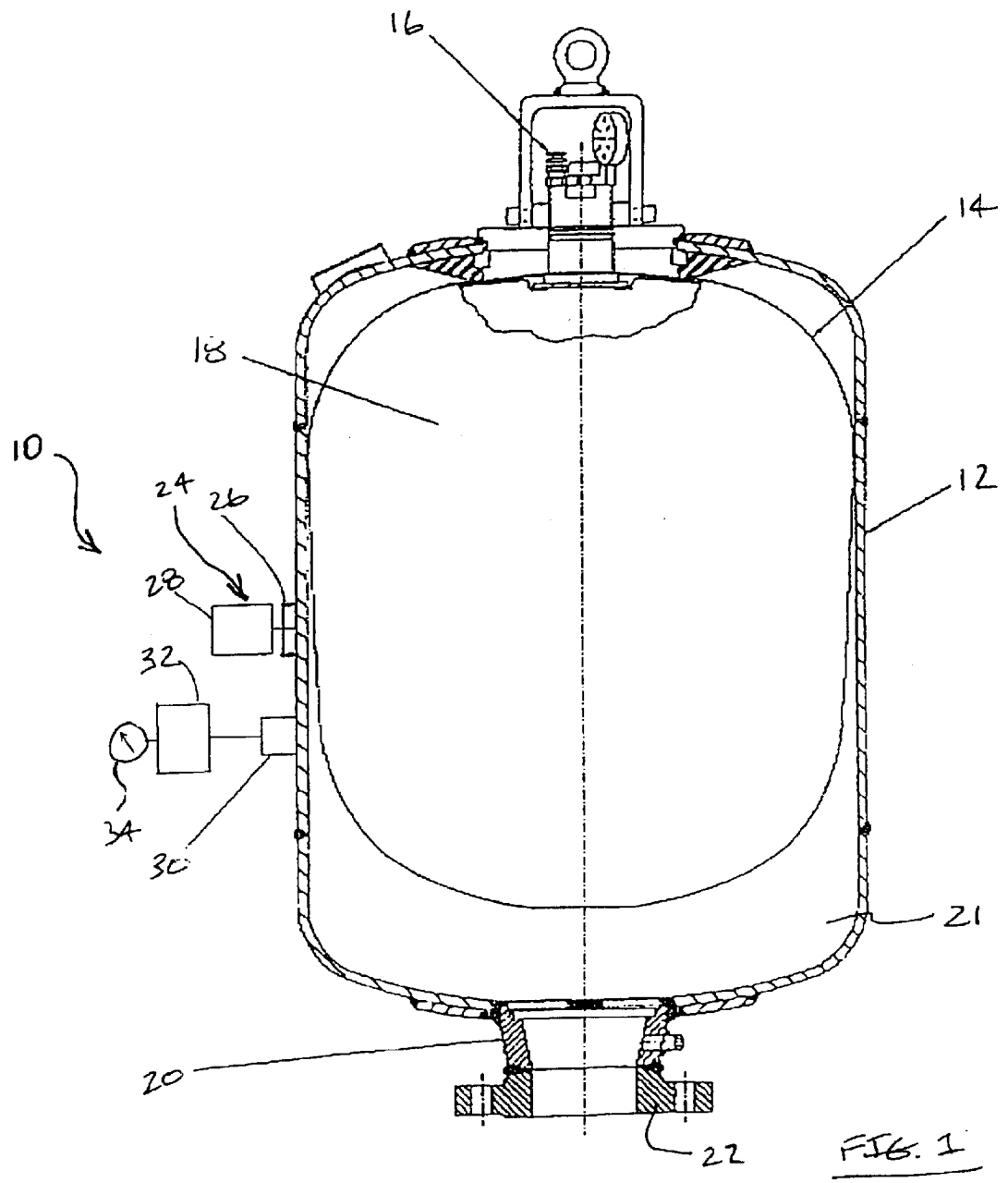
FIG. 1 is a schematic cross-sectional side elevation illustrating an acoustic volume indicator, constructed according to an embodiment of this invention, as used with a liquid volume container.

FIG. 1 is a schematic diagram illustrating an acoustic volume indicator 10 according to a first embodiment of this invention. As shown in FIG. 1, the indicator 10 is used to measure the liquid volume within a tank 12 that comprises an internal bladder 14 disposed therein. An example of such a tank is one used to suppress hydraulic surge that comprises a internal pressurized bladder or diaphragm for the purpose of accommodating a pressure surge or hydraulic transient in a fluid line that is connected thereto.

In such tank embodiment, the internal bladder 14 is disposed within an internal chamber of the tank, and services to separate liquid that enters and that is contained within the tank from compressed gas, in this case, air. The air is supplied from a pressurized source (not shown) through a valve 16, which is preferably molded to the bladder 14, and into a chamber 18 within the bladder 14. The valve 16 is positioned at one end of the tank. The bladder is sized and shaped to fit within the tank and to fully occupy the diameter of the tank when placed into a precharged condition. The tank includes a fluid inlet 20 at another end that is in fluid flow communication with the tank internal chamber 21. A flange or other conventional fluid transport coupling 22 is connected to the fluid inlet to direct liquid to the tank from an external source (not shown).

Although the indicator of this invention has been described and illustrated as being used to measure a liquid volume of a particular type of liquid container, it is to be understood that indicators of this invention can be used with a wide variety of liquid containers other than that specifically described and illustrated. Additionally, indicators of this invention can be used to not only measure the volume of liquid, but can be used to measure a volume of gas that has been compressed or pressurized to a liquid state. Thus, as used herein, the term liquid is understood to refer to the group of materials that are in a liquid state at ambient pressure, and to the group of gases that can be placed into a liquid state at elevated pressure.

The acoustic volume indicator 10 can be fixedly mounted to the tank, or can be provided as portable unit, i.e., packaged as a hand-held portable unit. The indicator 10 comprises means for causing the tank 12 to resonate or initiating tank resonation. In this indicator embodiment, such resonating means 24 is in the form of a device that can be positioned adjacent an outside wall of the tank, and that is configured having a member that physically contacts or otherwise impacts the tank wall. Alternatively, instead of using a mechanical device, the resonating means can be in the form of an electromechanical device capable or providing the desired vibrating motion without mechanically contacting or striking the tank wall.

In an example embodiment, where the resonating means is a mechanical device, the resonating means 24 is in the form of a contact 26, which is driven in a reciprocating manner through a solid connection by an electrical driver, such as a solenoid actuator 28. While a particular type of contactor has been described, it is be understood that other types of mechanical devices adapted to strike the tank wall in some way can be used. For example, a coil-type plunger or other device can be used to liquidly impact the tank being measured. The impact energy provided by the contactor is on the order of approximately 0.003 ft-lbs. The resonating means can include means for adjusting the impact energy provided therefrom. As better described below, the resonating means 24 can be activated by a controller to strike the tank in response to receiving a resonation initiating signal.

The system includes a means for sensing tank resonation caused by the resonating means 24. In this first embodiment indicator, such sensing means 30 can be any type of device that is capable of converting motion to an electrical impulse. In an example embodiment, sensing means is in the form of an accelerometer that is designed to detect and record for subsequent processing the vibration signal/signature of the tank generated by the resonating means. The sensing means is designed to respond to an increased amplitude of signals sensed at the resonant frequency of the tank.

The sensing means 30 provides the response signals to a detector and signal processor 32, which provides filtering, FFT or other processing, and which compares the response signal to preprogrammed specific frequency vs. volume characteristics of the tank. The signal processor 32 is designed for easy data input and is capable of storing hundreds of frequency vs. volume data, i.e., acoustic signatures, for all different tank shapes, sizes and pressures.

The detector and signal processor 32 are configured to convert the response signal obtained from sensing means 30 to a form usable by an output device or devices. In this example, the signal processor 32, after determining whether the response signal represents a quantity of liquid within a desired range by making the above comparison, produces an output to an visual indicator means 34, e.g., in the form of a gage. If the response signal indicates that the quantity of liquid within the tank is outside of the desired range, the indicator means 34 will respond accordingly. For example, the signal processor 32 can be preprogrammed to provide an output signal to a green light if the frequency of the tank is between a certain range (indicating a proper liquid volume in the tank), and provide an output signal to a red light if the frequency is outside of a certain range (indicating an improper volume in the tank.

Although the use of a particular type of indicating means has been described and illustrated, it is to be understood that the system can be adapted to provide a variety of different types of indication signals. For example, the system can be configured to provide an audible/warning signal in the event that a certain predetermined liquid level is not detected. This audible signal could be useful in the situation where the detected liquid level is above or below a predetermined danger set point, thus representing a warning alarm.

Additionally, the indicating means can be provided at a location remote from the tank, such as within a control room or the like.

In another embodiment, the acoustic volume indicator of this invention comprises a resonating means 24 that is designed to generate a sweep frequency vibration within the tank, instead of producing a momentary impact impulse. In an example embodiment, the resonating means is in the form of an electromechanical vibrator 28 that includes an impactor 26 configured to impact the wall of the tank 12 with a sweep frequency signal. The sweep frequency signal from the vibrator 28 is designed to cover a range of frequencies, which includes resonant frequencies between those resulting from impacting a full tank to those resulting from impacting an empty tank. The vibration provided by the vibrator 28 is transmitted through the wall of tank 12 to the liquid contained therein. Like the previous indicator embodiment discussed above, the resonating means of this indicator embodiment can be activated by a controller or other type of user operated or automatically operated initiating device.

A sensing means 30 is attached to the wall of the tank and is provided in the form of an accelerometer as discussed above for the previous embodiment indicator. The sensing means detects and records for processing the vibration signature of the tank as generated by the resonating means 24. The sensing means 30 is designed to sense an increased amplitude, when a resonant frequency occurs in the tank, and transmit this signal to a filter and signal processor 32. The signal processor 32 is designed to receive the response signal from the sensing means or accelerometer 30. The filter is designed to limit the signal processing to a frequency range representative of frequencies varying between those indicating a full tank to those indicating an empty tank. There will be a sharply increased amplitude signal sensed at the accelerometer 30 at each resonant frequency representing the current amount of liquid in tank 12.

The signal processor 32 is designed to operate in the manner described above for the previous indicator embodiment, i.e., to analyze and convert the data provided by the accelerometer and convert the time domain resonation signal to a frequency domain signal. The frequency domain signal is then compared to preprogrammed specific frequency vs. volume characteristics of the tank. Again, it is desired that the signal processor 32 be designed for easy data input, and be capable of storing hundreds of frequency vs. volume data, i.e., acoustic signatures, for all different tank shapes, sizes and pressures.

Like the previously described indicator embodiment, the detector and signal processor 32 of this other embodiment indicator is also configured to convert the response signal obtained from the sensing means 30 to a form usable by an output device or indicating means 34, e.g., a visual gage or other indicator, to indicate the quantity of liquid in the tank.

Again, as described for the earlier embodiment indicator, this other indicator embodiment can be configured to provide a variety of output signals. For example, rather that an output signal to an indicator gauge, the system can be adapted to provide an audible alarm signal in the event that the measured liquid level in the tank is above or below an alarm set point. Additionally, the indicator output can be provided to a location remote from the tank, e.g., to a control room if so required.

Although the indicating members described above have been illustrated in FIG. 1 in a particular manner, it is to be understood that this has been done for purposes of reference and example. If desired, the members can be grouped or combined differently than that shown. Additionally, the indicating members have been illustrated having a particular scale for purposes of easily identifying the same for reference, which scale may or may not be accurate of the invention as practiced.

In an example embodiment, acoustic liquid indicators of this invention are packaged in the form of a small electronic device capable of either being portable, i.e., hand held, or fixedly attached to the tank under test. The indicator has a portable, i.e., battery, operated power supply making use of commonly available battery sizes. The indicator comprises a housing that is made from suitable sturdy material, and is preferably of a weather-proof design. It is desired that the indicator be capable of exposure to ambient temperatures of from minus 20° F. to 120° F. with exposure to direct sunlight, and be designed for operation in ambient temperatures of from 30 to 110° F.

Figure 2:
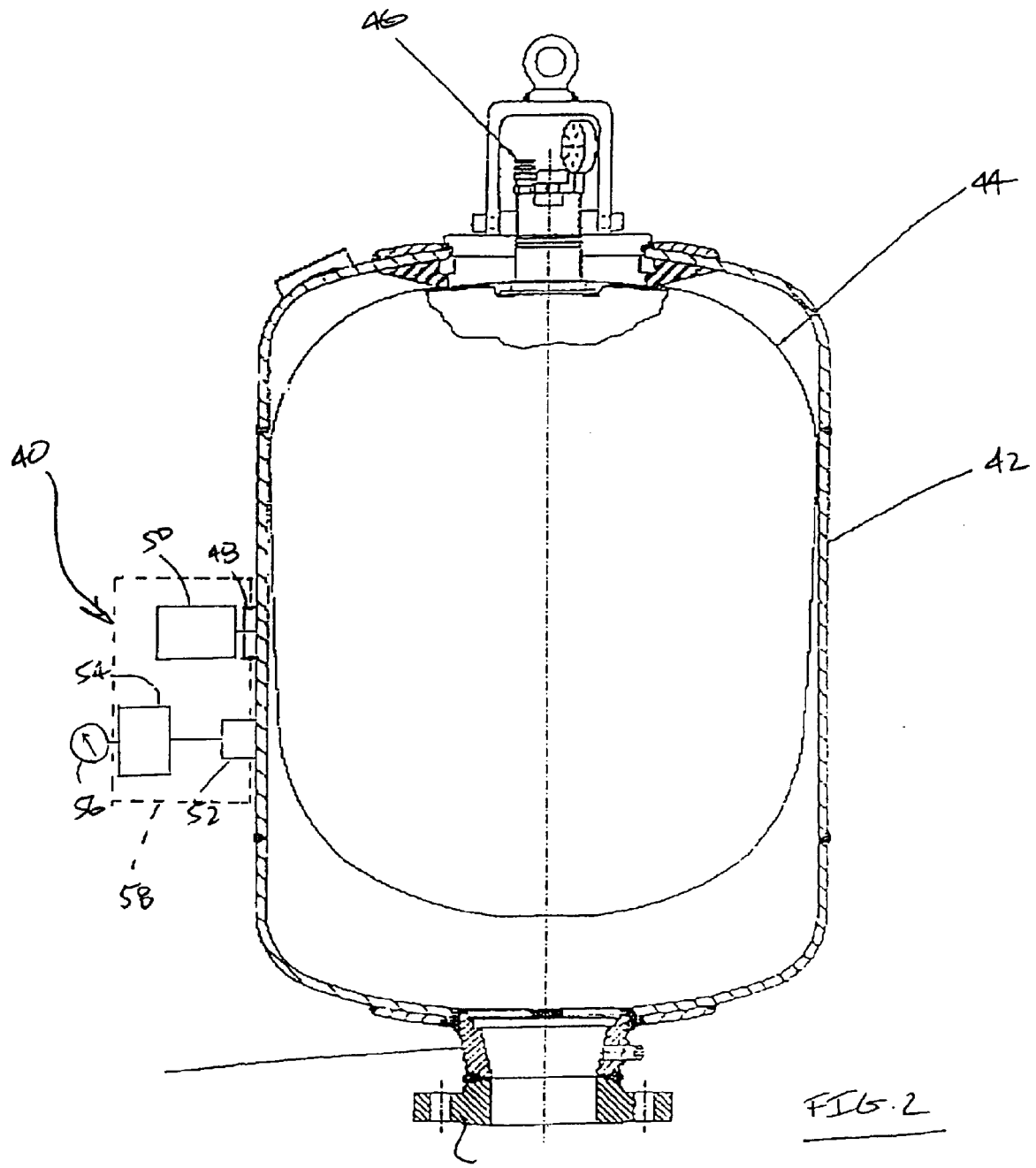
FIG. 2 is a schematic cross-sectional side elevation illustrating an acoustic volume indicator, constructed according to another embodiment of this invention.

FIG. 2 is a schematic diagram illustrating an acoustic volume indicator 40 constructed according to an embodiment of the invention as used with the same type of tank 42 described above for the indicator embodiment of FIG. 1. The tank 42 again comprising an internal gas pressurized bladder or diaphragm 44 having a gas charge valve 46 positioned through one end of the tank. The tank 42 includes a fluid inlet 48 at an opposite end that is configured to accommodate attachment with a fluid transport coupling 50.

This indicator is illustrated as having its components, i.e., the resonating means 48 and 50, the detecting means 52, the processing means 54, and indicating means 56 disposed or container within a common housing 58. The housing can contain the indicator members in such a manner as to promote portability of the indicator, or can contain the indicator members in such a manner as to provide a fixed indicator, depending on the particular application and use requirements.

Acoustic volume indicators of this invention comprises a number of different electrical circuits configured to operate the above-described different indicator members. In an example embodiment, the indicator comprises the following electrical circuits: (1) a power supply and regulation circuit; (2) a user control circuit; (3) a resonation excitation circuit; (4) a resonation detection circuit; (5) a resonation signal conditioning circuit; (6) a frequency detection circuit; and (7) a user display circuit.

The power supply and regulation circuit is designed to provide necessary voltage and current required for operation of the different indicator members, such as the resonating means, the sensing means, and the processing means. The power supply and regulation circuit is also used to provide necessary power to the other identified electrical circuits of the indicator.

In an example embodiment, user control over acoustic volume indicators of this invention is provided in the form of a power switch and a keypad. The power switch allows a user to turn on and turn off the indicator, so that energy can be conserved when the indicator is not in use. The user control circuit provides input from the keypad to a microprocessor in the indicator, so that the microprocessor can send power to the resonation excitation circuit. The keypad may also be used to reconfigure and/or tune the indicator to provide system flexibility, thereby enabling acoustic volume indication use across a wide range of measurement applications.

The resonation excitation circuit is used to activate the indicator resonating means to cause the tank under test to resonate. In an example embodiment, the resonation excitation circuit is implemented with a solenoid that when excited causes an impact to be made with the tank under test to initiate resonation. The resonation excitation circuit does not have to be limited to such a device, as it could be further implemented by nonphysical mechanical means such as by an acoustic coupling. Additional means for initiating tank resonation include magnetic, nuclear, strong or weak forces. Alternatively, this circuit could be removed from the indicator and provided by an external means for the purpose of exciting the tank into resonation.

The resonation detection circuit is used to convert the natural physical resonation of the tank, taken by the sensing means, into a form that can be processed for the detection of information content from the signal. In an example embodiment, the resonation detection circuit is provided by using a geophone that when the tank is excited causes an electrical signal that is proportional in frequency and amplitude to the mechanical resonance of the tank under test. The resonation detection circuit does not have to be limited to such a device, as it could be further implemented by non-acoustical mechanical means such as by physical coupling. Additionally, magnetic, nuclear, strong or weak forces could be used to implement tank resonation detection.

The resonation signal conditioning circuit is designed to condition the detection signal by amplification so that the following frequency detection circuit can operate properly. The frequency detection circuit is designed to convert the time domain resonation signal into a frequency domain signal. In an example embodiment, this conversion is done with a microprocessor-based device in conjunction with an analog-to-digital converter and DTF algorithms. The output of the algorithm is displayed on a liquid crystal display (LCD) and transmitted out of the serial port of the microprocessor for remote use.

The user display circuit is designed to provide a user with a visual indication of, but not limited to, test progress, system power condition, and tank volume based on detected resonation of the tank under test. The current implementation is done with an LCD, but is not limited to such as device.

Acoustic volume indicators of this invention are placed into volume indication operation by the user's act of engaging the user control noted above, e.g., by pressing one or more buttons on the keypad. This act activates the resonation excitation circuit, thereby causing the resonating means to initiate resonation of the tank. In the first embodiment indicator, this act causes energizes the solenoid 28 to activate the contactor or plunger 26 to impact the wall of the tank. In the other embodiment indicator, this act energizes the electromechanical vibrator 28 to activate the impactor 26.

The other circuits of the indicator are also activated, and the resonation detection circuit operates with the sensing means or accelerometer 30 to record the response to an impact signal and transfer the response data to the detector and signal processor 32 for processing such as FFT to determine the natural or resonant frequency of the tank 12. This frequency information is then compared in the signal processor 32 with the pre-programmed frequency vs. volume data via the frequency detection circuit, and an output signal is provided to a desired user display or indicator, e.g., a gage, as an indication of the liquid content in the tank.

A feature of acoustic volume indicators of this invention is that they enable measurement of liquid volume within a container in a noninvasive manner, which is important for volume measurements in such pressurized liquid containers as hydraulic surge suppressors. Another feature of acoustic volume indicators of this invention is that they can be provided in the form of a portable, handheld device, providing a desired degree in application flexibility.

The above-described embodiments of the present invention are merely descriptive of its principles and are not to be considered limiting. The scope of the present invention instead shall be determined from the scope of any claims in a corresponding non-provisional application, including their equivalents.

What is claimed is:

1. An acoustic volume indicator comprising:
    (a) a resonating means for vibrating a wall surface of a container comprising a volume of liquid disposed therein, and further comprising a bladder disposed within the container and in contact with the liquid, the bladder comprising a volume of pressurized gas therein, the resonating means being positioned noninvasively outside of the container and adjacent to the outside surface of the container wall surface;
    (b) a resonating detecting means for receiving vibration data from the container wall surface, the resonating detecting means being positioned noninvasively outside of the container and adjacent the container wall surface;
    (c) a frequency detection means for receiving a data signal from the detecting means, converting the data signal to frequency information, and comparing the frequency information to stored frequency and volume information for the container; and
    (d) an indicating means for providing a desired visual or audible output.

2. The acoustic volume indicator as recited in claim 1 wherein the resonating means is an impactor that vibrates the container wall surface by striking the container with an impulse.

3. The acoustic volume indicator as recited in claim 1 wherein the resonating means is an electromechanical vibration generator that vibrates the container wall surface by generating a sweep frequency.

4. The acoustic volume indicator as recited in claim 1 wherein the resonating detecting means is an accelerometer, and is adapted to record the received vibration data.

5. The acoustic volume indicator as recited in claim 1 wherein the frequency detection means comprises a microprocessor, and includes storage means for storing frequency and volume information for more than one liquid container.

6. The acoustic volume indicator as recited in claim 1 wherein the resonating means, resonating detecting means, and frequency detection means are all packaged within a common housing.

7. An acoustic volume indicator comprising:
    (a) an impactor for physically striking an outside surface of a liquid container with an impulse to momentarily vibrate the liquid container, the liquid container comprising a volume of liquid disposed therein, and further comprising an internal bladder disposed therein, the internal bladder comprising a volume of pressurized gas therein, the impactor being disposed noninvasively outside of the liquid container;
    (b) a detector for receiving and recording vibration information provided by the liquid container, the detector being positioned noninvasively outside of the liquid container;
    (c) a processor for receiving a data signal from the detector, converting the data signal to frequency information, and comparing the frequency information to stored frequency and volume information for the liquid container to determine the liquid volume in the liquid container; and (d) an indicator for providing an output indication of the determined liquid volume.

8. The acoustic volume indicator as recited in claim 7 wherein the detector is an accelerometer.

9. The acoustic volume indicator as recited in claim 7 further comprising storage means for storing frequency and volume information for more than one liquid container.

10. The acoustic volume indicator as recited in claim 7 wherein the impactor, detector, and processor are all packaged within a common housing.

11. An acoustic volume indicator comprising:

(a) a resonator positioned noninvasively adjacent an outside wall surface of a container to impose a sweep frequency onto the wall surface of the container, the container including a volume of liquid disposed therein;

(b) an accelerometer for receiving and recording vibration information provided by the liquid container, the accelerometer being positioned noninvasively outside of and adjacent to the wall a surface of container;

(c) a processor for receiving a data signal from the accelerometer, converting the data signal to frequency information, and comparing the frequency information to stored frequency and volume information for the container to determine the liquid volume in the container;

(d) storage means for storing frequency and liquid volume information for more than one container; and (e) an indicator for providing an output indication of the determined liquid volume;

(f) wherein the liquid container comprises a pressurized gas filled bladder disposed therein.

12. The acoustic volume indicator as recited in claim 11 wherein the resonator, accelerometer, processor, storage means, and indicator are all packaged within a common housing.

13. A fluid containment system comprising:

(a) a liquid container comprising a volume of liquid and a pressurized gas filled bladder disposed therein;

(b) a resonator for vibrating force an outside wall surface of the liquid container, the resonator being positioned noninvasively outside of the liquid container and adjacent to the outside wall surface;

(c) a detector for receiving and recording vibration information provided by the liquid container, the detector positioned adjacent noninvasively outside of the liquid container and adjacent to the outside wall surface of the liquid container;

(d) a processor for receiving a data signal from the detector, converting the data signal to frequency information, and comparing the frequency information to stored frequency and volume information for the liquid container to determine the liquid volume in the liquid container; and (e) an indicator for providing an output indication of the determined liquid volume.

14. A noninvasive method for measuring a liquid level within a liquid container comprising the steps of:

(a) vibrating an outside wall surface of the liquid container from a position outside of the liquid container, the liquid container comprising a volume of liquid disposed therein, and further comprising an internal pressurized gas filled bladder disposed therein;

(b) receiving vibration data from the liquid container by use of a device positioned outside of the container and in contact with the outside wall surface of the liquid container;

(c) converting the vibration data into frequency;

(d) comparing the frequency to stored frequency and liquid volume data for the liquid container to determine a liquid volume; and (e) providing an output indicative of the determined liquid volume.

15. The method as recited in claim 14 wherein the step of vibrating comprises striking the liquid container to cause a momentarily vibration.

16. The method as recited in claim 14 wherein the step of vibrating comprises generating a sweep frequency vibration in the liquid container.

17. The method as recited in claim 14 further comprising the step of storing the vibration data.

* * * * *